United States Patent [19]

Robyt et al.

[11] Patent Number: 6,031,085
[45] Date of Patent: Feb. 29, 2000

[54] ACTIVATED MONO,DI,OLIGO- AND POLYSACCHARIDES, REACTION PRODUCTS THEREOF, THEIR PREPARATION AND USES

[75] Inventors: John F. Robyt; Rupendra Mukerjea, both of Ames, Iowa

[73] Assignee: Iowa State University Research Foundation, Inc., Ames, Iowa

[21] Appl. No.: 09/058,888

[22] Filed: Apr. 13, 1998

Related U.S. Application Data

[62] Division of application No. 08/880,152, Jun. 20, 1997, Pat. No. 5,900,478.

[51] Int. Cl.$^7$ .......................... C08B 37/00; C08B 37/08; C08B 11/00; C08B 33/04; C08B 35/04
[52] U.S. Cl. ..................... 536/18.6; 536/20; 536/84; 536/111; 536/120; 536/123; 536/123.1; 536/123.13; 568/852
[58] Field of Search ................................. 536/18.5, 18.6, 536/20, 56, 84, 102, 103, 123, 123.1, 123.13, 111, 120; 568/852

[56] References Cited

U.S. PATENT DOCUMENTS

| | | | |
|---|---|---|---|
| 2,927,919 | 3/1960 | Anderson | 536/116 |
| 3,170,915 | 2/1965 | Gaertner | 536/120 |
| 3,300,474 | 1/1967 | Flodin | 536/120 |
| 4,335,100 | 6/1982 | Robyt et al. | 424/48 |
| 4,380,476 | 4/1983 | Mufti et al. | 127/46.3 |
| 5,122,601 | 6/1992 | Sachivala | 536/125 |
| 5,270,421 | 12/1993 | Dordick et al. | 527/311 |
| 5,498,709 | 3/1996 | Navia et al. | 536/124 |

FOREIGN PATENT DOCUMENTS

| | | |
|---|---|---|
| 1 543 167 | 3/1979 | France . |
| 366539 | 3/1976 | Spain . |
| 1543168 | 3/1979 | United Kingdom . |
| WO93/07159 | 4/1993 | WIPO . |
| WO94/27618 | 12/1994 | WIPO . |
| 98/03528 | 1/1998 | WIPO . |

OTHER PUBLICATIONS

Binder et al., *Carbodydrate Res.*, vol. 132(1): 173–177, 1984
Binder et al., *Carbohydrate Res.*, vol. 140(1): 9–20, 1985.
Eklund et al., *Carbohydrate Res.*, vol. 177(1):253–258, 1988.
Jezo et al., *Chem Zvesti*, vol. 25(5): 364–368, 1971.
Bolton et al., *Carbohydrate Res.*, vol. 21:133–143, 1972.
McKeown et al.—Selective Substitution in Sucrose—Canadian Journal of Chemistry, vol. 35, 1957, pp. 28–36.
Fariclough et al.—Derivatives of β–D–Fructofuranosyl α–D–Galacto–Pyranoside—Carbohydrate Research, 40 (1975) 285–298.
Bolton, et al.—Sucrochemistry—Part 1. New Derivatives of Sucrose Prepared from the 67,6'Di–O–Tosyl and the Octa–O–Mesyl Derivatives—Cabohyd. Res., 21 (1972) 133–143.

Chowdhary, et al.—Sucrochemistry. Part 33.The Selective Pivaloylation of Sucrose—J. Chem. Soc. Perkin Trans. I 1984, pp. 419–427.
Hirano et al.—Phosphorylated Glycans Produced from Non-reducing Mono–and Oligosaccharides by the Action of $P_2O_5$ in Dimethyl Sulfoxide and Their Interactions with Concanavalin A—Agr. Biol. Chem., 39 (10), 1963–1967, 1975.
Communications to the Editor—Journal of the American Chemical Society /87:30/ Oct. 20, 1965, pp. 4651–4652.
Khan—Chemistry of New Uses of Sucrose: How Important? —Pure & Appl. chem., vol. 56, No. 7, pp. 833–844, 1984.
Synthetic Polymers Containing Sugar Residues v. Polyesters Derived from D–Cellobiose and Dicarboxylic Acid Chlorides by Direct Polycondensation—Journal of Polymer Science: Polymer Chemistry Edition, vol. 18, 365–370 (1980).
Morris et al.—Experimental Chemical Shift Correlation Maps from Heteronuclear Two–Dimensional NMR Spectroscopy.. 1. Carbon–13 and Proton Chemical Shifts of Raffinose and Its Subunits—J. Am. Chem. Soc. 1981, 103, 4703–4711.
Ballard et al.—Sucrochemistry—Part 12. Reaction of Sucrose with Sulphuryl Chloride, J. Chem. Soc. Perkin I 1973, pp. 1524–1528.
Reactions of Aliphatic Acid Chlorides—N.O.V. Sonntag, Chem. Revs. 52 (1953) pp. 321–324.
Silver and Silver Alloys to Sulfolanes and Sulfones—Kirk–Othmer—Encyclopedia of Chemical Technology—Third Edition, vol. 21—pp. 921–948.
Collins and Ferrier, "Monosaccharides:Their Chemistry and Their Roles in Natural Products", pp. 355, 356 and 373–382, (1995).
Schotten—Article 547, p. 2544–2547—Chem. Ber. 17 (1884).
Baumann—Article 673, p. 3218–3220—Chem. Ber. 19 (1886).
Hinsberg—Article 475, p. 2962–2965—Chem. Ber. 23 (1890).
Hinsberg—p. 178–192—Ann. Chemic 265 (1991).
Foldi, Article 215, p. 1836–1839—Chem. Ber. 53 (1920).
Wu et al., "Goodeng Xuexiao Huaxue Xuebao", vol. 13(9): 1212–1216, (1992).
Shen et al., "Youji Hauxue", vol. 11(3):265–268 (1991).
Takahashi et al., "Tetrahedron Lett.", 25(31):3331–3334 (1984).

(List continued on next page.)

*Primary Examiner*—Howard C. Lee
*Attorney, Agent, or Firm*—McDermott, Will & Emery

[57] ABSTRACT

Reaction at the interface of an organic solution containing an acidic reactant and an aqueous alkaline solution containing nonreducing carbohydrates such as sucrose, sugar alcohols, cyclodextrins, and polysaccharides imparts a specificity to the reaction for one or more of the primary alcohol groups of the carbohydrate reactant. The resulting activated, nonreducing carbohydrate intermediate can then be converted to a series of substantially pure, low molecular weight reaction products, including a sucrose trimer and dianhydrosucrose, and to a series of substantially pure, higher molecular weight reaction products, including 6-O-sucro cyclodextrins and poly-6-O-sucro amylose.

55 Claims, No Drawings

OTHER PUBLICATIONS

Holzapfel et al., S. Afr. J. Chem., 37(2):57–61 (1984).

Patel et al., "Chem. Era", 14(1):30–32 (1978).

Hough, "Bifunctional Derivatives of Sucrose", *LaSucrerie Belge*, vol. 89, pp. 455–461 (1970).

Suami et al., "Crystalline 2,3,4,3'4'–penta–O–acetyl–6,1',6–tri–O–tosyl sucrose and its reactions", *Carbohydrate Research*, 19 (1971) 407–411.

Ball et al., "Synthesis of 6,1',6'Tri–O(Mesityl lenesulfonyl) Sucrose, Further Examination of 'Tri–O–Tosylsucrose', and the Chemistry of 3,6:1,4':4,6'–Trianhydrosucrose", *Carbohydrate Research*, 55 (1977) 149–163.

Ballard et al., "Selective tetratosylation of sucrose: isolation of the 2,6,1'6'–tetrasulphonate," *Carbohydrate Research*, 83 (1980) 138–141.

Guthrie et al., "1'–Derivatives of Sucrose and Their Acid Hydrolysis", *Aust. J. Chem*, 1980, 33, 2487–97.

Abstract of Japanese Application Publication 01051402, Patent Abstracts of Japan, European Patent Office.

6,031,085

ACTIVATED MONO,DI,OLIGO- AND POLYSACCHARIDES, REACTION PRODUCTS THEREOF, THEIR PREPARATION AND USES

This application is a division of application Ser. No. 08/880,152 filed Jun. 20, 1997, now U.S. Pat. No. 5,900,478.

FIELD OF THE INVENTION

This invention relates to new and useful sucrose derivatives, the particular methods for their syntheses, and the use of the products.

BACKGROUND OF THE INVENTION

The most abundant pure organic compound in the world is sucrose. See Kirk-Othmer, *Encyclopedia of Chemical Technology*, 3rd Edition, Volume 21, John Wiley & Sons, New York, pages 921–948 (1983). However, although sucrose produced from sugar cane and sugar beets is ubiquitous in its availability and is of relatively low cost, only a fraction of a percent by weight is consumed as a chemical feedstock. The potential value of sucrose as a raw material has been recognized for many years and has been the subject of considerable research.

Sucrose and assorted polyols, including polysaccharides, are particularly appropriate materials for use in the formation of esterified and etherified products produced currently from petroleum-based materials because they (a) are naturally occurring, relatively abundant renewable materials; (b) are polyfunctional with multiple reactive primary alcohols that can readily be derivatized; (c) are nonreducing carbohydrates and thus do not have the potential for the wide variety of side-reactions characteristic of reducing carbohydrates; (d) have relatively easily hydrolyzed glycosidic linkages that allow polymers made from such materials to be potentially more biodegradable than similar polymers made with hydrogenated carbohydrates, such as sugar alcohols; and (e) are naturally occurring products in common use and therefore potentially useful in the formation of novel ingredients for the food, beverage, pharmaceutical, and chemical industries.

SUMMARY OF THE INVENTION

It is an object of the invention described herein to provide novel methods for the preparation of substantially pure saccharide derivatives which are useful as food bulking agents, food dietary fibers, reduced calorie sweeteners, fat replacement materials, adhesives, thickening and emulsifying agents for food products, biodegradable plastics and films, sizing agents for paper and textiles, ethical pharmaceuticals, new dentifrices, and new fibers.

A further object of the present invention is the provision of a method for preparing polysaccharide derivatives in high yields and with improved specificity as compared to methods known to the prior art.

An even further object of the invention is to provide a method for the preparation of activated sucrose, activated sugar alcohols, activated oligosaccharides, or activated polysaccharides in substantially pure forms which have facile leaving groups at multiple primary hydroxyl positions, thus providing activated reactants which can be used to synthesize a number of additional new products.

An even further object of the present invention is to provide activated sucrose, activated sugar alcohol, activated oligosaccharide, or activated polysaccharide intermediates wherein the activated sucrose, activated sugar alcohol, activated oligosaccharides, or activated polysaccharide intermediate can be reacted with another molecule including single or multiple saccharides so as to form a novel series of highly useful products.

In satisfaction of the foregoing objects and advantages, the present invention provides in one embodiment a method for preparation of an activated polysaccharide by reaction of the polysaccharide with a reactant which will provide a facile leaving group, e.g. tosyl (p-toluenesulfonyl) or trityl (triphenylmethyl), at various primary hydroxyl groups of the polysaccharide. The reaction is conducted by adding a tosyl or trityl halide contained in a water-immiscible organic solvent to the polysaccharide contained in an alkaline aqueous solution, and recovering the product.

In a main embodiment, the present invention provides substantially pure sulfonyl substituted nonreducing mono-, di-, oligo- and polysaccharides, wherein the monosaccharides are represented by the sugar alcohols such as xylitol and glucitol, the disaccharides are represented by sucrose, the oligosaccharides are represented by the cyclodextrins, and the polysaccharides are represented by cellulose, amylose, amylopectin, pullulan, and chitosan and their lower molecular weight analogs.

The present invention also provides activated sucrose intermediate products containing facile leaving groups at the 6- and 6'-positions of sucrose, and methods for conversion of the activated sucrose intermediate products by a condensation reaction with other molecules, e.g., mono-, di-, tri-, oligo- and polysaccharides, to produce substantially pure condensed sucrose products which are novel and highly useful materials.

The present invention further provides activated sugar alcohol intermediate products containing facile leaving groups at the primary hydroxyl positions of the sugar alcohol, and methods for conversion of the activated sugar alcohol intermediates by a condensation reaction with other molecules, e.g., mono-, di-, tri-, oligo- and polysaccharides, to produce substantially pure condensed sugar alcohol products which are novel and highly useful materials.

Also provided by the present invention are sucrose products substituted at the 6- and 6'-positions, and sugar alcohol, oligosaccharide, and polysaccharide products substituted at various primary methylene positions by substituents such as halogen, amino, carboxylic acid esters, etc., such products being formed by reaction of the activated sucrose, sugar alcohol, oligosaccharide, or polysaccharide with an appropriate reactant which will effect nucleophilic displacement.

Other objects and advantages of the present invention will become apparent as the description thereof proceeds.

DETAILED DESCRIPTION OF THE INVENTION

The present invention involves reactions of certain reagents with polysaccharides, oligosaccharides, sugar alcohols or sucrose, the latter having the following structure and, numbering system for the reactive hydroxyl groups and corresponding carbon atoms:

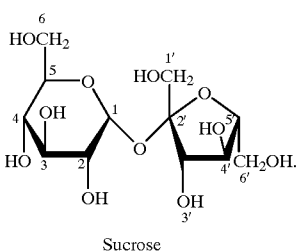

Formula 1

Sucrose

Through the reactions of this invention it has been discovered that one can direct the specificity of the reactions to the 6- and 6'-positions of sucrose, and corresponding equivalent positions within sugar alcohols, oligosaccharides, and polysaccharides, and thus form activated sucrose, sugar alcohols, oligosaccharides, or polysaccharides which are important intermediates in the preparation of a novel and useful series of sucrose, sugar alcohol, oligosaccharide, or polysaccharide reaction products, and also in the formation of other useful derivatives. Because the reactions are very specific, the activated sucrose, sugar alcohol, oligosaccharide, or polysaccharide is substantially pure, and unwanted side products are avoided.

According to the present invention, both low molecular weight products and high molecular weight products can be produced. Low molecular weight products are produced from disaccharides such as sucrose and sugar alcohols such as alditols and pentitols.

Low Molecular Weight Reaction Products

By use of a two-phase reaction system, the processes of the present invention in a major embodiment produce "activated sucrose" and "activated sugar alcohols" which have facile sulfonyl leaving groups at the activated primary hydroxyl positions. Because of the relatively low cost and ready availability of tosyl chloride, tosyl is the most economical facile leaving group. While tosyl is the preferred leaving group, other sulfonyl groups may also be used. While the reaction is effective with nonreducing carbohydrates in general, the present invention is described herein with respect to sucrose and sugar alcohols as the preferred starting materials.

The present invention provides a procedure by which the 6-, 6'-, and/or 1'-positions of sucrose, and one or more of the primary alcohol groups within sugar alcohols, can be activated or made reactive in a specific manner so that a wide series of new sucrose and sugar alcohol products can be produced. The new sucrose products contain such linkages that these new products are useful as food bulking agents providing properties characteristic of sucrose. The new sucrose reaction products are also noncaloric and noncariogenic. The new sugar alcohol products contain linkages that make these new products useful as food and non-food materials requiring properties characteristic of sugar alcohols.

The present invention provides three significant new types of products, i.e., a. activated sucrose and activated sugar alcohols by substitution of one or more tosyl or trityl groups on the primary alcohols within the activated sucrose or activated sugar alcohol;

b. reaction of the activated sucrose with sucrose or various sugar alcohols, or reaction of the activated sugar alcohol with sucrose or with the same or different sugar alcohol, to form sucrose-sucrose, sucrose-sugar alcohol, sugar alcohol-sucrose, or sugar alcohol-sugar alcohol condensation products connected by ether linkages; and c. reaction, by nucleophilic displacement, of the activated sucrose or activated sugar alcohol with a reactive halogen, carboxylic acid, amine, or ester to form halogen-, carboxylic acid-, amino-, ester-, or anhydro- substituted sucrose, or halogen-, carboxylic acid-, amino-, or ester-substituted sugar alcohols.

The experiments herein show that a facile or active group can be selectively added to one or more of the primary hydroxyl positions of sucrose or sugar alcohols, by using a two-phase reaction in which the facile-group reactant is dissolved in a water-immiscible solvent such as toluene and slowly added to an aqueous alkaline solution of sucrose or sugar alcohol. When TLC (thin layer chromatography) analysis of the aqueous layer shows that all of the sucrose or sugar alcohol has been consumed, TLC analysis of the solvent layer will show a single, UV-fluorescent carbohydrate derivative indicating that the reaction is complete. The presence of the activated sucrose or sugar alcohol can also be determined by $^{13}$C-NMR which also indicates that facile leaving groups are positioned at specific primary hydroxyl positions.

The "activated sucrose" of the invention is demonstrated herein by the use of a tosylation reaction and specifically the use of tosyl chloride. Tosyl is the preferred leaving group because of its low cost and ready availability. However, other sulfonyl groups may be used in the reaction with substantially the same results. Suitable sulfonyl derivatives that will form sulfonates with alcohols such as sucrose and sugar alcohols comprise tosyl chloride, which yields tosylates; mesyl chloride (methyl sulfonyl chloride) which yields methyl sulfonates or mesylates; trifyl chloride, ($\alpha,\alpha,\alpha$-trifluoromethyl sulfonyl chloride) which yields trifluoromethane sulfonates or trifylates; trimsyl chloride (mesitylene chloride or 2,4,6-trimethyl benzene sulfonyl chloride) which yield 2,4,6-trimethyl benzene sulfonates or mesitylates; tripsyl chloride, (2,4,6,-triisopropyl benzene sulfonyl chloride) which yields 2,4,6-triisopropyl benzene sulfonates or tripsylates; and 1,1'-sulfonyldiimidazole, which yields imidazylates or imidazolesulfonates. In general, any sulfonyl derivative which is operative under the conditions of the reaction may be used.

Non-sulfonyl substituents such as trityl may also be added to sucrose by reaction with trityl chloride.

It should be noted that sulfonyl, such as tosyl, and trityl derivatives however react by different mechanisms. Tosyl is a leaving group because it activates any hydroxyl group to which it is bonded during formation of the corresponding p-toluenesulfonyl ester. Trityl on the other hand, is not a leaving group and is not displaceable. The trityl group protects selected, generally primary, hydroxyl groups thus allowing other reactions to take place at non-tritylated hydroxyl groups within the molecule. Trityl can then be removed by acid to free the hydroxyl group or groups to which it had been attached.

In a further embodiment, the 6,6'-di-O-tosyl sucrose is an activated form of sucrose that can be used to synthesize specific sucrose analogues by nucleophilic displacement of the tosyl groups, giving, for example, 6,6'-dichloro-; 6,6'-dibromo-; 6,6'-di-iodo-; 6,6'-diamino-; 6, 6'-dideoxy-; 6,6'-dicarboxymethyl sucrose and the like in high yield. The preparation of the tosyl sucrose derivative on a simple, but large scale, holds the potential for synthesizing a number of sucrose derivatives and analogues that would have variable uses as food bulking agents and anticariogenic agents among others.

The activated intermediate sucrose products of the invention may be characterized by the following formula:

Formula 2

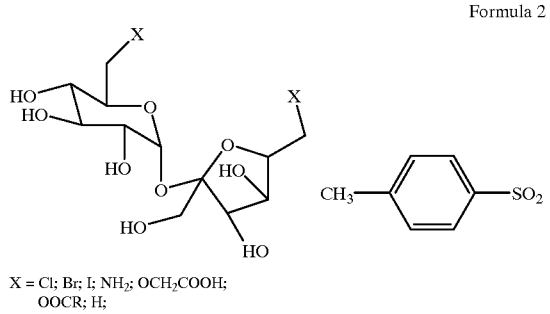

X = Cl; Br; I; NH$_2$; OCH$_2$COOH;
OOCR; H;

wherein X is a facile leaving group as indicated at the 6- and 6'-positions and preferably is a tosyl group or the like. As discussed herein, the groups other than tosyl are added to sucrose at its 6- and 6'-positions by nucleophilic displacement of the tosyl or similar groups.

As indicated above, the activated sucrose products of Formula 2 are intermediates ideally suited for production of a wide variety of sucrose condensation products. Such sucrose products may be described by the general formula:

Formula 3

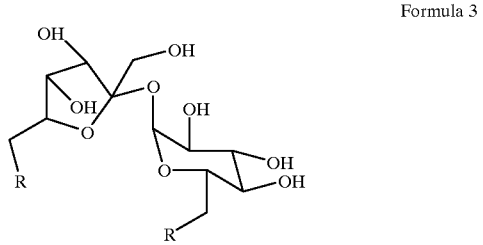

In the above formula, R represents any organic moiety which can be attached to sucrose by displacement of the tosyl or equivalent groups at the 6- and 6'-positions of "activated sucrose". Thus, each R group can be another sucrose moiety (sucrose trimer), sugar alcohols such as glucitol or xylitol, or polysaccharides or their lower molecular weight analogs (see High Molecular Weight Reaction Products section).

As noted, sucrose is the starting material when forming "activated sucrose". However, various sugar alcohols may be used in place of sucrose to form a series of "activated sugar alcohols" and their corresponding reaction products. Such equivalent sugar alcohols include glucitol, mannitol, xylitol, and the like.

According to this invention, it has been discovered that conducting the reaction of sucrose or various sugar alcohols with a sulfonyl derivative such as a tosyl halide as described herein, enables one to obtain specificity of the reaction at the 6-and 6'-positions of sucrose or at one or both of the primary hydroxyl groups of the sugar alcohols. The resulting products are sulfonyl substituted sucrose or sugar alcohols wherein a sulfonate, e.g., a tosyl ester, is substituted at the 6- and 6'-positions of sucrose or at multiple methylene sites within the various sugar alcohols.

An especially novel feature of the invention concerns the method by which the sucrose or sugar alcohol products of the present invention are produced. According to the invention, it has been discovered that sucrose substituted at its 6- and 6'-positions, or sugar alcohols substituted at one or both of their primary hydroxyl groups, by a sulfonyl derivative, e.g., tosyl, can be produced in high yield and purity by conducting the reaction with two substantially immiscible solvents. The process is conducted generally by dissolving the appropriate amount of sucrose or sugar alcohol in a slightly alkaline aqueous medium and then adding slowly thereto a sulfonyl halide such as a tosyl halide reactant contained in a substantially water-immiscible organic solvent. Organic solvents which may be used in the reaction comprise such solvents as chlorinated aliphatic hydrocarbons such as chloroform and carbon tetrachloride; aromatic hydrocarbons such as benzene, toluene, and xylene; and chlorinated aromatic hydrocarbons such as chlorobenzene.

It should be understood that the process for reaction of sucrose or a sugar alcohol with the reagents disclosed herein has wide applicability to the production of new sucrose and sugar alcohol reaction products. The concept of conducting the reaction at the interface of two substantially immiscible solvents containing the reactants provides a novel and effective procedure for producing the sucrose and sugar alcohol reaction products with the unexpected result of avoiding the substantial formation of unwanted products or by-products. The reaction is exemplified by the reactions and products described herein but is not limited thereto.

In a preferred mode of conducting the reaction, the solution of the sulfonating agent in the organic phase is added slowly, preferably dropwise over a period of up to about one hour, to an aqueous alkaline solution of sucrose or sugar alcohol to produce a derivative easily recovered from the aqueous phase. Further, the organic phase can be separated and recycled for use in subsequent reactions.

Sucrose or specific sugar alcohol added to the aqueous phase is utilized at a concentration of about 5 wt. % up to the limit of its solubility at the temperature used. Ordinarily, a concentration of 5–50% by weight is employed. Likewise, the reactant in the organic phase is employed at a concentration of about 5 wt. % up to the limit of its solubility in the solvent at the temperature used, but preferably using a concentration in the range of 5–50 wt. %. To obtain specific derivatives, the concentration may be varied by increasing the amount of organic solvent and/or by decreasing the rate of dropwise delivery of the reactant to the alkaline solution of sucrose or specific sugar alcohol.

While the ratios of reactants are ordinarily stoichiometric, the ratios of organic phase reactant to sucrose, or sugar alcohol, may be varied from 1:2 to about 4:1, preferably about 1.2:1 to 2.2:1. Alkali is provided at a concentration of 0.05 to 5 molar, preferably 0.1 molar. The reaction takes place in a relatively short period of time, such as one half hour to 3 hours. However, occasionally the reaction is allowed to continue overnight. This is possible because room temperature is suitable for conducting the reaction, although 0° to 80° C., preferably 5° to 50° C., is also useful.

The process of the invention results in the production of an "activated sucrose" or "activated sugar alcohols" which contain facile leaving groups at the 6- and 6'-positions of sucrose or the primary alcohol positions of the reacted sugar alcohol. In a preferred embodiment, a sulfonyl group such as a tosyl group is selectively added to the 6- and 6'-positions of sucrose by using the said two-phase reaction in which tosyl chloride is dissolved in a solvent such as toluene and added slowly to the aqueous, alkaline solution of sucrose. As indicated, this reaction results in sucrose substituted at its 6- and 6'-positions by tosyl groups. Tosyl is the preferred substituent because of economics and availability, but it is clear from the description herein that other active sulfonyl derivatives such as mesyl chloride or the like can be employed in the reaction. However, the availability and low costs of tosyl chloride make it eminently suitable for the reaction of the invention.

In an important further embodiment of the invention, the activated sucrose containing tosyl groups at its 6- and 6'-positions is exceedingly useful as an intermediate to synthesize new sucrose condensation products. Such new products include dianhydrosucrose, sucrose dimers and trimers, and sucrose linked to carbohydrates of varying molecular configurations and of varying molecular weights up to and including polysaccharides.

Similar condensations may be obtained by adding 6,6'-di-O-tosyl sucrose, i.e., "activated sucrose" (dissolved in a solvent such as toluene), to an aqueous, alkaline solution of other carbohydrates, such as sugar alcohols. Depending on the ratio of sugar alcohol to 6,6'-di-O-tosyl sucrose, two different types of products are obtained. A 1:1 ratio of sugar alcohol to 6,6'-di-O-tosyl sucrose gives preference to the formation of a cyclic 6,6'-sugar alcohol-sucrose, and a 2:1 ratio gives preference to the formation of a linear 6,6'-di-O-sugar alcohol-sucrose.

In a similar manner, primary alcohol groups of sugar alcohols may be activated by the addition of tosyl groups following dropwise addition of tosyl chloride in a solvent such as toluene to aqueous, alkaline solutions of sugar alcohols. The 1,6-di-O-tosyl-alditols, e.g., glucitol, or corresponding 1,5-di-O-tosyl-pentitols, e.g., xylitol, dissolved in toluene, added to an aqueous, alkaline solution of sucrose, provides displacement of the tosyl groups and condensation of sucrose with the two primary alcohol ends of the alditol or pentitol.

In a particularly preferred embodiment of the invention, 6,6'-di-o-tosyl sucrose can be specifically converted, in high yield and purity, into 3,6;3',6'-dianhydrosucrose by refluxing the tosyl sucrose in an anhydrous lower alkyl alcohol, e.g. dry methanol, with catalytic amounts of an alkali methyl alkoxide, e.g., sodium methoxide. The reaction produces high conversion into 3, 6; 3',6'-dianhydrosucrose that can be crystallized.

When the same reaction is conducted at a temperature of about 60° C., a relatively large yield of 3,6;3',6'-dianhydrosucrose in high purity is obtained in the aqueous phase, along with smaller amounts of two monoanhydrosucroses, presumably 3,6-anhydrosucrose and 3',6'-anhydrosucrose. These three anhydrosucrose compounds can be separated on a silica gel column, using the filtering column technique. The first fractions contain carbohydrate, corresponding by TLC to 3,6;3',6'-dianhydrosucrose. This compound crystallizes when the first fractions of column eluant are pooled.

When 6,6'-di-O-tosyl sucrose, the compound obtained in the toluene phase at 20° C., is dissolved in methanol with the addition of a catalytic amount of sodium methoxide and the solution refluxed for 24 hours, a single carbohydrate results, as judged by TLC. This compound migrates at the same position on TLC as the 3,6;3',6'-dianhydrosucrose produced in the aqueous, alkaline phase of the 60° C. reaction. This compound, derived from 6,6'-di-O-tosyl sucrose, can be crystallized from an alcohol, preferably ethanol. The form of the crystals is the same as that of the crystals formed in the column chromatography eluant.

Each of the compounds, that is, the one recovered from the aqueous phase of the 60° C. reaction of tosyl chloride in toluene with an aqueous solution of sucrose, and the one recovered from refluxing 6,6'-di-O-tosyl sucrose in methanol/sodium methoxide, have specific optical rotation of +6.8° in water. Further, neither of the reactions affords a product which is oxidized by sodium periodate.

In the known prior art [Lemieux and Barrette, *Canadian Journal of Chemistry*, vol. 37 (1959) 1964–1969 and Bolton, et al., *Carbohydrate Research*, vol. 21 (1972) 133–143] dianhydrosucrose has been reported. However, according to said prior art, the dianhydrosucrose has been produced neither in pure form nor in any large quantities. Thus, the production of 6,6'-di-O-tosyl sucrose, in the two-phase reaction of the invention, is ideal to form 3,6;3',6'-dianhydrosucrose in a substantially pure form, in high yields, and in large quantities.

3,6;3',6'-Dianhydrosucrose is a nonmetabolizable bulking agent, retaining many of the properties of sucrose. Its structure is depicted as follows:

Formula 4

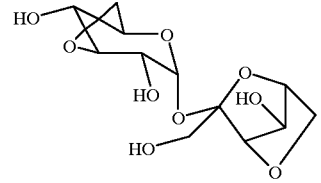

Several different types of sucrose and sugar alcohol products are contemplated by this invention: (1) synthesis of a specific tosylated sucrose, e.g., 6,6'-di-O-tosyl sucrose; (2) synthesis of specific tosylated sugar alcohols, e.g., 1,6-di-O-tosyl glucitol; (3) synthesis of sucrose condensed with sucrose and linked together by ether linkages to give a trimer, denominated "sucrotriose"; (4) reaction of sugar alcohols with "activated sucrose" to link sugar alcohols to sucrose at its C-6 and C-6' positions by ether bonds to give both cyclic 6,6'-sugar alcohol-sucroses and linear 6,6'-di-O-sugar alcohol sucroses; (5) reaction of a 1,6-di-O-tosyl alditol or a corresponding 1,5-di-O-tosyl pentitol with sucrose to give sucrose attached to the alditol or pentitol by ether linkages between positions 6 or 6' of sucrose and either primary hydroxyl group of the alditol or pentitol; (6) reaction of a 1,6-di-O-tosyl alditol or a corresponding 1,5-di-O-tosyl pentitol with a variety of sugar alcohols to link the selected sugar alcohol by ether bonds between either primary hydroxyl group of the selected sugar alcohol and either primary hydroxyl group of the di-O-tosylated alditol or pentitol; and (7) synthesis of specific anhydrosucrose products, e.g., 3,6;3',6'-dianhydrosucrose.

As indicated above, the "activated sucrose" and "activated sugar alcohols" of the invention contain facile leaving groups, such as tosyl, and are eminently suitable for reaction with a wide array of reactants to produce a range of substituted sucrose and sugar alcohol products. Thus, in one embodiment, "activated sucrose" may be reacted with various reagents to form, by nucleophilic displacement, a series of new sucrose products which contain 6- and 6'-substituents such as Cl, Br, I, $NH_2$, $OCH_2COOH$, OOCR, and H. These sucrose products are formed by reaction of "activated sucrose" with reagents such as sodium chloride to substitute chloride groups at the 6- and 6'-positions in high yield and good purity. Similar reactions may be conducted with sodium bromide, sodium iodide, ammonia, acetic acid, or the like. This results in a pathway by which multiple substituted sucrose products can be produced.

Additional objects and advantages of the present invention will become readily apparent to those skilled in the art from the following examples which exemplify the low molecular weight products of this invention and their methods of preparation. As will be realized, the invention is capable of other and different embodiments, and its several details are capable of modifications in various obvious respects, all without departing from the invention.

EXAMPLE 1

Synthesis of 6,6'-di-O-tosyl sucrose

Sucrose (10 g, 29.2 mmol) was dissolved in 50 mL of 0.1 M NaOH. Tosyl chloride (12.3 g, 64.2 mmol) was dissolved in 50 mL of toluene and added to the sucrose solution over 30 minutes at 22°. The pH of the reaction was maintained between 7 and 8. The 6,6'-di-O-tosyl sucrose migrates into the toluene phase where it is detected by TLC analysis [one ascent in methyl cyanide/water (85/15, v/v) on Whatman K5 plates] as a UV-fluorescent compound that also gives a carbohydrate stain when the TLC plate is dipped into a solution containing 0.3% (w/v) N-(1-naphthyl)ethylene diamine and 5% (v/v) concentrated sulfuric acid in methanol, followed by drying and heating at 120° C. for 10 minutes. The toluene phase was rotary evaporated to give a syrup containing the product.

EXAMPLE 2

Reaction of sucrose with 6,6'-di-O-tosyl sucrose

Sucrose (10 g, 29.2 mmol) was dissolved in 100 mL of 0.1 M NaOH. 6,6'-Di-O-tosyl sucrose (7 g, 14.6 mmol) was then dissolved in 100 mL of toluene and added to the aqueous sucrose solution over 30 minutes at 22° C. The product, a sucrose trimer denominated sucrotriose, appeared in the aqueous phase. TLC of the aqueous and toluene phases is performed as previously described to verify product formation and location.

EXAMPLE 3 a. Preparation of 3,6;3',6'-dianhydrosucrose

Crystalline 6,6'-di-O-tosyl sucrose (8.3 g, 17.3 mmol) was dissolved in 200 mL of dry methanol. The temperature was slowly increased until the solution began to reflux and sodium methoxide (1.75 g, 32.4 mmol) was added in small portions over 30 minutes. The solution was refluxed 24 hours. TLC [one ascent in acetonitrile/water (85:15, v/v) on Whatman K5 plates] showed one compound. Water (200 mL) is added and the solution rotary evaporated to a syrup under vacuum at 35OC. The syrup was redissolved in 150 mL of water and neutralized with 0.1 M HCl, treated with charcoal (2 g) and filtered. The filtrate was rotary evaporated to a solid and dissolved in 200 mL of warm ethanol and filtered; the remaining solid (primarily salts) was treated with 100 mL of dry ethanol. The ethanol extracts are combined and rotary evaporated to a solid, which is the 3,6;3',6'-dianhydrosucrose. This solid was dissolved in a minimum amount of hot ethanol, and crystals obtained.

6,6'-Di-O-tosyl sucrose (2 g, 4.2 mmol) was dissolved in 50 mL of methanol and sodium methoxide (350 mg, 6.5 mmol) added. The solution was allowed to reflux for 24 hours. TLC analysis (10 cm Whatman KS plates with one ascent in acetonitrile/water, 85:15 v/v) showed a single compound migrating in the same location as 3,6;3',6'-dianhydrosucrose. The methanol solution was rotary evaporated to a syrup, which was dissolved in water, filtered and neutralized with a small volume of 1 M HCl. The aqueous solution was rotary evaporated to a syrup, which was dissolved in methanol and warmed; the insoluble material (salts) was removed by filtration. The solution was rotary evaporated to a syrup. The syrup was dissolved in 100 mL hot ethanol and concentrated to a volume of 50 mL. Crystals start to form in 12 hours at room temperature. The crystals are dissolved in water before TLC analysis and measurement of the specific optical rotation.

b. Separation of anhydrosucroses by silica gel, filtering column chromatography

The mixture of anhydrosucroses present in the aqueous phase of the above reaction following its rotary evaporation to a syrup was washed several times with acetone before a final wash with ethanol to give a solid, anhydrous powder. Approximately 10 g of this solid was dissolved in 10–15 mL of water. Solid silica gel (500 mg) was added, and the mixture rotary evaporated to remove the free water. This silica gel-carbohydrate adsorbed material was added to the top of a silica gel column (5.5×30 cm), and the compounds eluted (100-mL fractions) with different proportions of acetonitrile/water: 100:0 (1L); 99:1 (2L); 98:2 (1L); and 96:4 (2L). 3, 6;3',6'-Dianhydrosucrose was recovered from the 96:4 eluant. On standing at room temperature (20°–21° C.), the compound crystallized in the pooled 96:4 eluant. Specific optical rotation was measured, and a TLC analysis performed.

EXAMPLE 4

Synthesis of sucrose-sugar alcohol compounds from sugar alcohol and 6,6'-di-O-tosyl sucrose.

a. 1:1 Ratio of sugar alcohol to 6,6'-di-O-tosyl sucrose using the alditol, D-glucitol, as the example.

D-Glucitol (also known as D-sorbitol) (10 g, 55 mmol) was dissolved in 50 mL 0.1M NaOH; 6,6'-di-O-tosyl sucrose (26.5 g, 55 mmol) was dissolved in 50 mL toluene and added to the aqueous D-glucitol solution over 30 minutes at 22° C. Reaction progress was monitored and confirmed by TLC. Although D-glucitol was used as the example, other alditols, such as D-mannitol, and pentitols, such as D-xylitol, may be substituted for D-glucitol. The reaction is shown as follows:

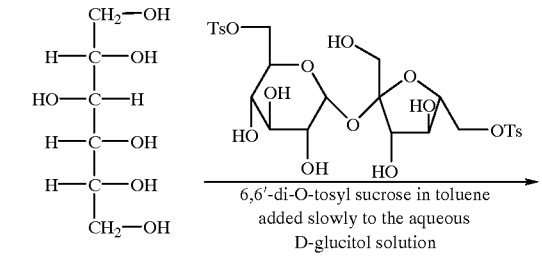

D-glucitol in 0.1 M NaOH

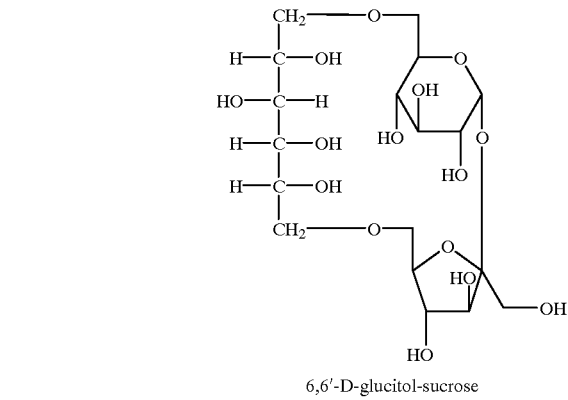

6,6'-D-glucitol-sucrose where Ts=p-toluenesulfonyl.

Formula 5. Synthesis of 6,6'-D-glucitol sucrose.

b. 2:1 Ratio of sugar alcohol to 6,6'-di-O-tosyl sucrose using the alditol, D-glucitol, as the example.

D-Glucitol (10 g, 55 mmol) was dissolved in 50 mL 0.1 M NaOH; 6,6'-di-O-tosyl sucrose (13.3 g, 27.6 mmol) was dissolved in 50 mL toluene and added to the aqueous D-glucitol solution over a period of 30 minutes at 22° C. TLC was performed as before. The reaction is shown as follows:

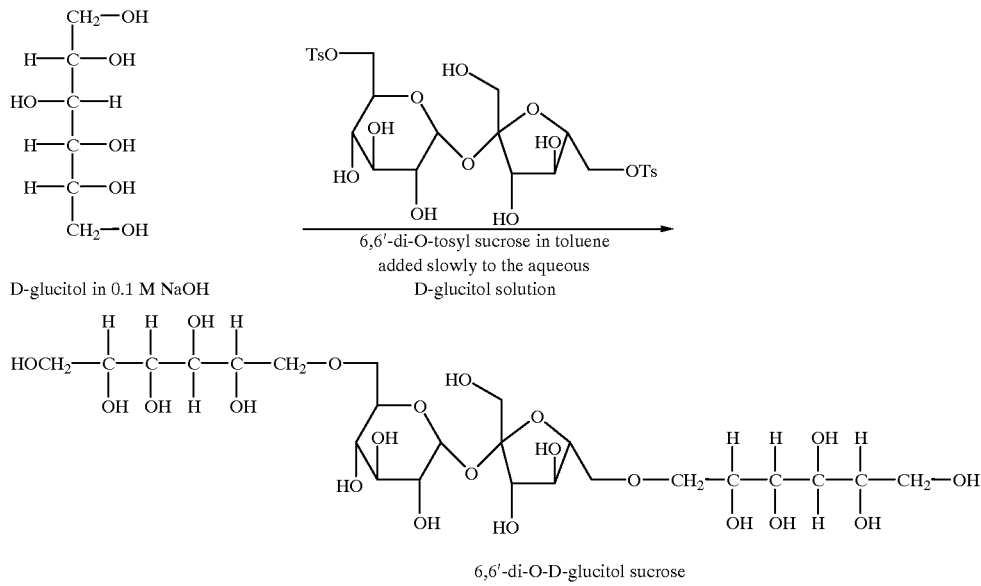

where Ts=p-toluenesulfonyl

Formula 6. Synthesis of 6,6'-di-O-D-glucitol sucrose.

EXAMPLE 5

Synthesis of 1,6-di-O-tosyl-D-glucitol.

D-glucitol (10 g, 55 mmol) was dissolved in 100 mL of 0.1 M NaOH. Tosyl chloride (23.3 g, 121 mmol) was dissolved in 100 mL of toluene and added to the aqueous D-glucitol solution over 30 minutes at 22° C. The reaction was monitored by TLC using the method described above. The 1,6-di-O-tosyl D-glucitol appeared in the toluene phase and was UV-fluorescent on TLC plates. The reaction was permitted to proceed for 18 hours at 22° C. Although D-glucitol was used as the example, other alditols, such as D-mannitol, and pentitols, such as D-xylitol, may be substituted for D-glucitol.

EXAMPLE 6

Synthesis of 1,6-di-O-sucro D-glucitol.

Sucrose (20 g, 58.4 mmol) was dissolved in 100 mL of 0.1M NaOH. 1,6-Di-O-tosyl D-glucitol (14.4 g, 29.2 mmol) was dissolved in 100 mL of toluene and added to the aqueous sucrose solution over 30 minutes at 22° C. The product was soluble in the aqueous phase. The reaction was permitted to proceed for 18 hours, being monitored by TLC. Although D-glucitol was used as the example, other alditols, such as D-mannitol, and pentitols, such as D-xylitol, may be substituted for D-glucitol.

EXAMPLE 7

Synthesis of 4,1'-dichloro-4,1'-dideoxy-galacto-sucrose.

6,6'-Di-O-tosyl sucrose (20 g, 31 mmol) was treated with sulfuryl chloride in chloroform and pyridine to form 4,1'-dichloro-4,1'-dideoxy-6,6'-di-O-tosyl-galacto-sucrose. This was reacted with aqueous sodium hydroxide to the corresponding 4,1'-dichloro-4'-dideoxy-galacto-sucrose.

EXAMPLE 8

Synthesis of 6,1',6'-tri-O-trityl sucrose.

Sucrose (25 g, 73 mmol) was dissolved in 250 mL of 1M NaOH. trityl chloride (46 g, 165 mmol) was dissolved in 250 mL of toluene and added slowly over 5 hours at 22° C. to the sucrose solution with constant stirring. The reaction was stirred at 22° C. for an additional 12 hours. The pH of the reaction was maintained between 7 and 9, with the optimum at 8, by the addition of aqueous NaOH (20% w/v). The toluene phase was separated from the alkaline phase and washed with 100 mL of water. TLC [one ascent in methanol/acetone/water/chloroform (20:20:3:57 v/v/v/v), Whatman K5 plate] of the toluene phase indicated one, fast migrating compound with an $R_f$ corresponding to 6,1',6'-tri-O-trityl sucrose. (See Otake, Bull. Chem. Soc. Japan 43: 3199, 1970). The toluene layer was dried with anhydrous sodium sulfate, filtered, and rotary evaporated at 50° C. to a solid 35.3 g). Only one compound was shown by TLC, indicating a high yield and a high degree of purity.

EXAMPLE 9

Synthesis of chloro-deoxy-galacto-sucrose products.

a. 6,1',6'-Tri-O-trityl-2,3,4,3',4'-penta-O-acetyl sucrose.

6,1',6'-Tri-O-trityl sucrose (30g, 28 mmol; TTS) dissolved in 480 mL of anhydrous pyridine. Acetic anhydride (300 mL) was added, and the solution was stirred for 20 hours at 22° C. The reaction solution was poured under vigorous stirring into 3 L of ice-water containing 153 mL of acetone, and stirred until all the ice was melted. A white precipitate was formed and recovered by filtration. The recovered precipitate was washed with water (5×20 mL) and dried under vacuo at 40° C. to give 29.4 g of pure, fully acetylated TTS.

b. 2,3,6,3',4'-Penta-O-acetyl sucrose.

Fully acetylated TTS (10 g, 8 mmol) was dissolved in 250 mL of glacial acetic acid. The solution was heated to boiling and 5 mL of water were added. The solution was allowed to reflux for 30 minutes. After cooling to 22° C., the reaction mixture was filtered and rotary evaporated at 50° C. to remove the acetic acid. Pure, 2,3,6,3',4' -penta-O-acetyl sucrose (9.4 g) was recovered. During detritylation, the acetyl group at position-4 migrates to position-6 (see Formula 1).

C. 2,3,6,3',4'-Penta-O-acetyl-4,1',6'-trichloro-4,1',6'-trideoxy-galacto-sucrose.

2,3,6,3',4'-Penta-O-acetyl sucrose (9 g, 16 mmol) was dissolved in a mixture of pyridine (250 mL) and chloroform (30 mL), previously cooled to −78° C., in an acetone-dry ice bath. Sulfuryl chloride (27 mL), previously cooled to −78° C., was added dropwise under vigorous stirring over a 45-minute period. The stirring reaction was maintained at −78° C. for 2 hours, allowed to warm to 22° C., and stirred for an additional 48 hours. TLC [one ascent in chloroform/ethanol (30:1 v/v), Whatman K5F plate] indicated one major, fast migrating product. The pyridine solution was rotary evaporated to give 2,3,6,3',4',-penta-O-acetyl-4,1',6'-trichloro-4,1',6'-trideoxy-galacto-sucrose. Authenticity of the recovered product was determined by proton-decoupled $^{13}$C-NMR. Reaction of 2,3,6,3',4'-penta-O-acetyl sucrose with sulfuryl chloride in pyridine to synthesize the trichloro derivative was accompanied by inversion of the pyranose portion of sucrose from a gluco to a galacto configuration.

d. 4,1',6'-Trichloro-4,1',6',-trideoxy-galacto-sucrose.

2,3,6,3',4'-Penta-O-acetyl-4,1',6'-trichloro-4,1',6'-trideoxy-galacto-sucrose (6.3 g, 10 mmol) was dissolved under stirring in methanol (300 mL) sodium methoxide (0.6 g) was added, and the reaction was stirred at 22° C. for 10 hours. Deacetylation with sodium methoxide in methanol afforded 4,1',6'-trichloro-4,1',6'-trideoxy-galacto-sucrose (Sucralose™).

EXAMPLE 10

Synthesis of 4-Chloro-4-deoxy-galacto-sucrose.

In a manner similar to Example 9(c) above, 6,1',6'-tri-O-trityl sucrose was reacted with sulfuryl chloride in a pyridine-chloroform solution and in the presence of an acid. 4-Chloro-4-deoxy-galacto-sucrose was recovered as a pure product.

It has been shown [Hough and Khan, Trends in *Biological Science*, vol. 3 (1978) 61–63] that the monochloro sucrose derivative is four times sweeter than sucrose, the dichloro derivative is 600 times sweeter than sucrose, and the trichloro derivative is 2000 times sweeter than sucrose.

High Molecular Weight Reaction Products

By use of the same two-phase reaction system, the processes of the present invention in a major embodiment produce "activated oligosaccharides" and "activated polysaccharides" which have sulfonyl facile leaving groups such as tosyl at the activated primary hydroxyl positions. Because of the relatively low cost and ready availability of tosyl chloride, tosyl is the most economical facile leaving group. While the reaction is effective with nonreducing carbohydrates in general, the present invention is described herein with respect to oligosaccharides or polysaccharides as the preferred starting materials.

This embodiment of the invention provides a procedure by which some of the primary alcohol groups within oligosaccharides or polysaccharides can be activated or made reactive in a specific manner so that a wide series of new oligosaccharide or polysaccharide products can be produced. The new products contain ether linkages so that the new products are useful as food and non-food agents which require properties characteristic of polysaccharides or their lower molecular weight analogs. Substituting sucrose and/or sugar alcohols onto poly-saccharides such as amylose and cellulose increases their water-solubility so that the resulting polysaccharide products are more useful as fibers, gels, gums, and films for foods and pharmaceuticals.

The present invention provides three significant new types of products, i.e., a. activated polysaccharides by substitution of a sulfonyl group on one or more of the primary alcohols within the reacted polysaccharide;

b. reaction of the activated polysaccharide with sucrose or with different sugar alcohols to form polysaccharide-sucrose or polysaccharide-sugar alcohol condensation products connected by ether linkages; and c. reaction, by nucleophilic displacement, of the activated polysaccharide with a reactive halogen, carboxylic acid, amine, or ester to form halogen-, carboxylic acid-, amino-, or ester-substituted polysaccharides.

The experiments herein show that a facile or active group can be selectively added to various primary methylene positions in oligosaccharides or polysaccharides, by using a two-phase reaction in which the facile-group reactant is dissolved in a water-immiscible solvent such as toluene and slowly added to an aqueous alkaline solution of oligosaccharide or polysaccharide. When TLC analysis shows that all of the starting material has been consumed, TLC analysis will show a single, UV-fluorescent carbohydrate derivative indicating that the reaction is complete.

The "activated oligosaccharide" or "activated polysaccharide" of the invention is demonstrated herein by the use of a tosylation reaction and specifically the use of tosyl chloride. Tosyl is the preferred leaving group because of its low cost and ready availability. However, other sulfonyl halides such as mesyl chloride may be used in the reaction with substantially the same results as is discussed above with respect to the low molecular weight products of this invention.

In this embodiment, the poly-6-O-tosyl saccharides are activated forms that can be used to synthesize specific analogues by nucleophilic displacement of the sulfonyl groups, giving, for example, poly-6-chloro-; poly-6-bromo-; poly-6-iodo-; poly-6-amino-; poly-6-deoxy-; poly-6-carboxymethyl derivatives of oligo- and polysaccharides in high yield. The preparation of poly-tosyl oligo- or polysaccharide on a simple, but large scale, holds the potential for synthesizing a number of derivatives and analogues that would have variable uses as food and non-food ingredients.

As noted in the previous section, sucrose and various sugar alcohols are the starting materials when forming "activated sucrose" and "activated sugar alcohols", respectively. However, various oligo- or polysaccharides may be used in place of sucrose or sugar alcohols to form a series of "activated oligosaccharides" or "activated polysaccharides". Such equivalent saccharides consist of the cyclodextrins, cellulose, amylose, amylopectin, pullulan, chitosan and the like. Since these equivalent polysaccharides are usually insoluble in aqueous media, a pyridine solution is used to expedite the reactions as described hereinafter.

As noted in the previous section, the R group of Formula 3 can be a polysaccharide, e.g., amylose, cellulose, amylopectin, chitosan, pullulan, the cyclodextrins, etc., or their lower molecular weight analogs.

According to this invention, it has been discovered that conducting the reaction of oligosaccharides or polysaccharides with a sulfonyl group such as a tosyl halide as described herein, enables one to obtain specificity of the reaction at multiple primary hydroxyl groups within the oligo- or polysaccharide. The resulting products are poly-tosyl-substituted reaction products wherein tosyl or other sulfonyl groups are substituted at multiple methylene sites within the oligosaccharide or polysaccharide.

An especially novel feature of the invention concerns the method by which the oligo- and polysaccharide products of the present invention are produced. According to the invention, it has been discovered that oligo- and polysaccharides substituted at multiple primary hydroxyl positions by e.g., tosyl groups, can be produced in high yield and purity by conducting the reaction with two substantially immiscible solvents. The process is conducted generally by dissolving the appropriate amount of oligosaccharide or polysaccharide in a slightly alkaline aqueous medium and then adding slowly thereto a sulfonyl reactant, such as a tosyl chloride, contained in a substantially water-immiscible organic solvent. Organic solvents which may be used in the reaction comprise such solvents as chlorinated aliphatic hydrocarbons such as chloroform and carbon tetrachloride; aromatic hydrocarbons such as benzene, toluene, and xylene; and chlorinated aromatic hydrocarbons such as chlorobenzene.

It should be understood that the process for reaction of oligo- or polysaccharides with the reagents disclosed herein has wide applicability to the production of new reaction products. The concept of conducting the reaction at the interface of two substantially immiscible solvents containing the reactants provides a novel and effective procedure for producing the high-molecular-weight saccharide reaction products with the unexpected result of avoiding the substantial formation of unwanted products. The reaction is exemplified by the reactions and products described herein but is not limited thereto.

In a preferred mode of conducting the reaction, the solution of the sulfonating reagent, e.g., tosyl chloride, in the organic phase is added slowly, preferably dropwise, over a period of up to about one hour, to an aqueous alkaline solution of oligo- or polysaccharide to produce a derivative easily recovered from the aqueous phase. Further, the organic phase can be separated and recycled for use in subsequent reactions.

The oligo- or polysaccharide added to the aqueous phase is utilized at a concentration of about 5 wt. % up to the limit of its solubility at the temperature used. Ordinarily, a concentration of 5–50% by weight is employed. Likewise, the reactant in the organic phase is employed at a concentration of about 5 wt. % up to the limit of its solubility in the solvent at the temperature used, but preferably using a concentration in the range of 5–50 wt. %. To obtain specific derivatives, the concentration may be varied by increasing the amount of organic solvent and/or by decreasing the rate of dropwise delivery of the reactant to the alkaline solution of oligosaccharide or polysaccharide.

While the ratios of reactants are ordinarily stoichiometric, the ratios of organic phase reactant to oligo- or polysaccharide may be varied from 1:2 to about 4:1, preferably about 1.2:1 to 2.2:1. Alkali is provided at a concentration of 0.05 to 5 molar, preferably 0.1 molar. The reaction takes place in a relatively short period of time, such as one half hour to 3 hours. However, occasionally the reaction is allowed to continue overnight. This is possible because room temperature is suitable for conducting the reaction, although 0° to 80° C., preferably 5° to 50° C., is also useful.

The process of the invention results in the production of an "activated oligosaccharide" or an "activated polysaccharide" which contains facile leaving groups at multiple primary hydroxyl positions of the reacted oligo- or polysaccharide. In a preferred embodiment, a tosyl group is selectively added to multiple primary hydroxyl positions of oligo- or polysaccharides by using said two-phase reaction in which tosyl chloride is dissolved in a solvent such as toluene and added slowly to the aqueous, alkaline solution of high-molecular-weight saccharide. As indicated, this reaction results in substitution at multiple methylene positions by tosyl groups. Tosyl is the preferred substituent because of economics and availability, but it is clear from the description herein that other active materials such as mesyl chloride or the like can be employed in the reaction. However, the availability and low costs of tosyl chloride makes it eminently suitable for the reaction of the invention.

In an important further embodiment of the invention, the activated oligosaccharide or the activated polysaccharide containing tosyl or similar groups at multiple primary hydroxyl positions is eminently useful as an intermediate to synthesize new oligo- or polysaccharide condensation products.

Experiments have shown that several poly-6-O-tosyl-polysaccharides (e.g., cellulose, amylose, amylopectin, pullulan, chitosan) and poly-6-O-tosyl oligosaccharides (e.g., the cyclodextrins) can be formed and are insoluble in both the aqueous and organic phases. They are, however, soluble in pyridine. Therefore, in this reaction, an aqueous, alkaline solution of sucrose is added to a pyridine solution of the poly-6-O-tosyl-polysaccharide or the poly-6-O-tosyl oligosaccharide. The sucrose will displace the tosyl groups to give a polysaccharide or oligosaccharide chemically bonded to the 6- or 6'-positions of sucrose by ether linkages at its primary methylene sites originally bearing the tosyl groups.

In a similar manner, sugar alcohols may be added to an "activated oligosaccharide" or an "activated polysaccharide". The selected sugar alcohol will displace the tosyl groups in the poly-tosylated starting material to give a product in which the selected sugar alcohol is chemically bonded at either of its primary hydroxyl positions by ether linkages at the primary methylene sites originally bearing the tosyl groups.

Several different types of high-molecular-weight-saccharide products are contemplated by this invention: (1) synthesis of sulfonyl substituted poly-saccharides, e.g., poly-6-O-tosyl amylose, or their lower molecular weight analogs; (2) reaction of poly-tosylated polysaccharides, or their lower molecular weight analogs, with sucrose to give high molecular weight products in which sucrose is attached by ether linkages between either position 6 or 6' of sucrose and the primary methylene positions at which the tosyl groups were originally bonded; (3) reaction of poly-tosylated polysaccharides, or their lower molecular weight analogs, with sugar alcohols to give high molecular weight products in which sugar alcohols are attached by ether linkages between either primary hydroxyl position of the sugar alcohol and the primary methylene positions at which the tosyl groups were originally bonded; and (4) synthesis of sulfonyl substituted oligosaccharides, e.g., β-cyclodextrin, for reaction with sucrose and/or sugar alcohols as described in (2) and (3) above.

As indicated above, the "activated oligosaccharides" and "activated polysaccharides" of the invention contain facile leaving groups, such as tosyl or mesyl, and are eminently suitable for reaction with a wide array of reactants to produce a range of substituted products.

EXAMPLE 9

Synthesis of poly-6-O-tosyl polysaccharides and their reaction with sucrose.

a. Synthesis of poly-6-O-tosyl cellulose.

Alpha-cellulose or micro-crystalline cellulose (10 g, 62 mmol anhydroglucose) was dissolved in 20 mL Cadoxen (5% cadmium oxide in 28% aqueous ethylenediamine). After dissolution (ca. 15 minutes), the Cadoxen-cellulose solution was diluted with water to 100 mL. Tosyl chloride (4 g, 20.7 mmol) was dissolved in 100 mL of toluene and added to the Cadoxen-cellulose solution over 30 minutes at 22° C. Tosyl cellulose became insoluble in both the aqueous and organic phases. Samples of tosyl cellulose are obtained by centrifugation of the aqueous phase followed by dissolution in pyridine. The reaction was monitored by determining the amount of UV-fluorescence on a TLC plate. The maximum UV-fluorescence indicates the maximum synthesis of tosyl cellulose.

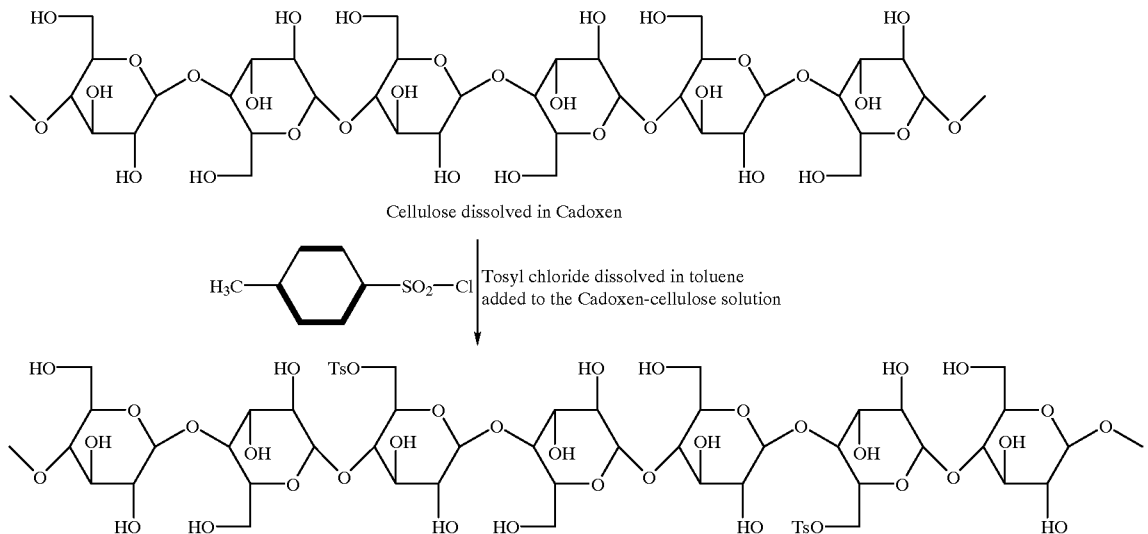

Cellulose dissolved in Cadoxen

Tosyl chloride dissolved in toluene added to the Cadoxen-cellulose solution where Ts=p-toluenesulfonyl Formula 7. Preparation of poly-6-O-tosyl cellulose.

b. Synthesis of poly-6–0-tosyl amylose.

Amylose (10 g, 62 mmol anhydroglucose) was dissolved in 10 mL dimethyl sulfoxide (DMSO) under stirring and gentle warming (ca. 50° C.). After dissolution, the DMSO-amylose solution was diluted with 0.1 M NaOH to 100 mL. Tosyl chloride (4 g, 20.7 mmol) was dissolved in 100 mL of toluene and added to the aqueous amylose solution over 30 minutes at 22° C. Tosyl amylose becomes insoluble in both the aqueous and organic phases. Tosyl amylose, obtained by centrifugation of the aqueous phase, was dissolved in pyridine. The reaction was monitored by determining the amount of UV-fluorescence by TLC. The maximum UV-fluorescence indicates the maximum synthesis of tosyl amylose. The reaction is similar to that of forming the poly-6-O-tosyl cellulose.

c. Synthesis of poly-6-O-tosyl amylopectin, pullulan, and chitosan.

Each of these polysaccharides (10 g) was dissolved in 100 mL of 0.1 M NaOH. Tosyl chloride (4 g, 20.7 mmol) was dissolved in 100 mL of toluene and added to the aqueous polysaccharide solutions over 30 minutes at 22° C. Each tosyl polysaccharide becomes insoluble in both the aqueous and organic phases. A sample of each tosylated polysaccharide was obtained by centrifugation of the aqueous phase followed by dissolution in pyridine. The reaction was monitored by determining the amount of UV-fluorescence by TLC. The maximum UV-fluorescence demonstrated that maximum synthesis of the tosyl polysaccharide has taken place.

d. Attachment of sucrose to each of the poly-6-O-tosyl polysaccharides.

Poly-6-O-tosyl polysaccharide (12–14 g, d.s.=0.24–0.33) was dissolved in 100 mL of pyridine. Sucrose (5 g, 14.6 mmol) was dissolved in 100 mL of 0.1 M NaOH and added to the poly-6-O-tosyl polysaccharide-pyridine solution over 30 minutes at 50° C. Reaction progress was monitored by TLC by relating the consumption of sucrose with the loss of fluorescence at the origin using the method described above. The poly-6-O-sucro polysaccharides are soluble in the aqueous-pyridine solution. They are recovered by the addition of two volumes of ethanol. The reaction shown below is for the formation of poly-6-O-sucro-cellulose, but similar equations may be written for amylose, amylopectin, pullulan and chitosan, and their lower molecular weight analogs, and for the cyclodextrins.

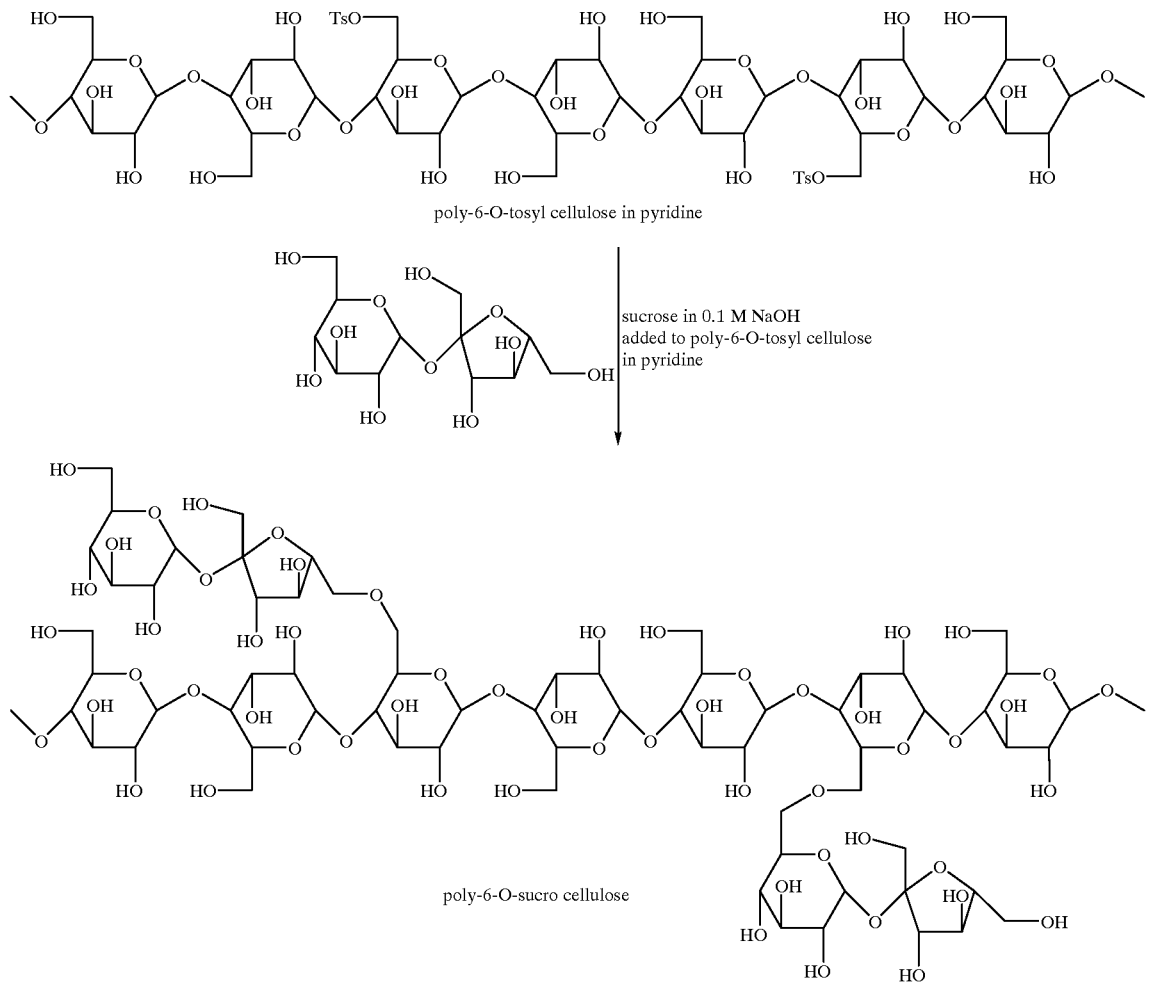

where Ts=p-toluenesulfonyl

Formula 8. Preparation of poly-6-O-sucro-cellulose.

The invention has been described herein with reference to certain preferred embodiments. However, as obvious variations thereon will become apparent to those skilled in the art, the invention is not to be considered as limited thereto.

What is claimed is:

1. Sucrose linked through its 6- or 6'-positions to one or more primary hydroxyl group of sugar alcohols, sucrose, cyclodextrins, or polysaccharides or their lower molecular weight analogs.

2. A sucrose according to claim 1 which is linked to a primary hydroxyl position of a sugar alcohol selected from the group consisting of the alditols and pentitols.

3. A sucrose according to claim 1 which is a sucrose trimer.

4. A sucrose according to claim 1 linked through its 6- or 6'-positions to multiple primary hydroxyl groups of cyclodextrins.

5. A sucrose according to claim 1 linked through its 6- or 6'-positions to multiple primary hydroxyl groups of polysaccharides selected from the group consisting of cellulose, amylose, amylopectin, chitosan and pullulan, and their lower molecular weight analogs.

6. A sucrose according to claim 2 which is a cyclic 6,6'-sugar alcohol-sucrose, where the sugar alcohol is selected from the group consisting of alditols and the pentitols.

7. A sucrose according to claim 2 which is a linear 6,6'-di-O-sugar alcohol-sucrose, wherein the sugar alcohol is selected from the group consisting of the alditols and the pentitols.

8. A process for the preparation of a series of alditol or pentitol sugar alcohol-sucrose products which comprises slowly adding 6,6'-di-O-tosyl sucrose in a substantially water-immiscible organic solvent to a pentitol or an alditol sugar alcohol in an alkaline solution of the sugar alcohol, wherein a reaction takes place at the interface of the alkaline solution and the organic solution, and maintaining the reaction until the alditol or pentitol sugar alcohol-sucrose product is produced.

9. The process of claim 8, wherein the organic solvent containing 6,6'-di-O-tosyl sucrose is added to aqueous sugar alcohol solution in a dropwise manner.

10. The process of claim 8, wherein the organic solvent is a chlorinated organic solvent or an aromatic solvent.

11. The process of claim 8, wherein the organic solvent is selected from the group consisting of methylene chloride, chloroform, carbon tetrachloride, benzene, toluene, or a xylene.

12. The process of claim 8, wherein the sugar alcohol is present in the alkaline aqueous solution in a concentration of about 5% by weight up to the limit of solubility of the sugar alcohol in water.

13. The process of claim 8, wherein the concentration of 6,6'-di-O-tosyl sucrose in the water-immiscible organic solvent is from about 5% by weight up to the limit of solubility of the 6,6'-di-O-tosyl sucrose in the solvent.

14. The process of claim 8, wherein the molar ratio of 6,6'-di-O-tosyl sucrose in the organic phase reactant to sugar alcohol reactant in the aqueous solution is from about 1:1 to about 1:4.

15. The process of claim 8, wherein the reaction is conducted at a temperature in a range of about 0° to about 80° C.

16. The process according to claim 15, wherein the molar ratio of 6,6'-di-O-tosyl sucrose to sugar alcohol is about 1:1 to about 1:1.1, the reaction is conducted at a temperature of about 15° to about 25° C., and at a pH of about 7.5 to about 10.5, and the organic solution of the 6,6'-di-O-tosyl sucrose reactant is added to the sugar alcohol solution over a period of about 15 to about 45 minutes.

17. The process according to claim 15, wherein the molar ratio of 6,6'-di-O-tosyl sucrose to sugar alcohol is about 1:1 to about 1:2.2, the reaction is conducted at a temperature of about 15° to about 25° C., and at a pH of about 7.5 to about 10.5, and the organic solution of the 6,6'-di-O-tosyl sucrose reactant is added to the sugar alcohol solution over a period of about 15 to about 45 minutes.

18. A cyclic sugar alcohol-sucrose produced by the process of claim 16 which is 6,6'-D-glucitol sucrose.

19. A linear sugar alcohol-sucrose produced by the process of claim 17 which is 6,6'-di-O-D-glucitol sucrose.

20. A product produced by the process of claim 8.

21. A process for the preparation of a series of pentitol and alditol sugar alcohol reaction products which comprises slowly adding a substantially water-immiscible organic solvent containing a sulfonyl reactant to an alkaline, aqueous solution of a sugar alcohol, wherein a reaction takes place at the interface of the aqueous solution and the organic solution, and maintaining the reaction until a sulfonyl sugar alcohol reaction product is produced.

22. The process of claim 21, wherein the sulfonyl reactant is selected from the group consisting of tosyl chloride, mesyl chloride, trifyl chloride, trimsyl chloride, tripsyl chloride, or 1,1'-sulfonyl diimidazole.

23. The process of claim 21, wherein reaction conditions are controlled so that the tosyl reactant selectively reacts with the sugar alcohol at one or both of the primary hydroxyl groups in the sugar alcohol molecule.

24. The process of claim 21, wherein the organic solvent solution containing the tosyl reactant is added to the aqueous sugar alcohol solution in a dropwise manner.

25. The process of claim 21, wherein the organic solvent is a chlorinated organic solvent or an aromatic solvent.

26. The process of claim 25, wherein the organic solvent is selected from the group consisting of methylene chloride, chloroform, carbon tetrachloride benzene, toluene, or a xylene.

27. The process of claim 21, wherein the sugar alcohol is present in the alkaline aqueous solution in a concentration of about 5% by weight up to the limit of solubility of the sugar alcohol in water.

28. The process of claim 21, wherein the concentration of the tosyl reactant in the water-immiscible organic solvent is from about 5% by weight up to the limit of solubility of the tosyl reactant in the solvent.

29. The process of claim 21, wherein the molar ratio of tosyl reactant in the organic phase to sugar alcohol in the aqueous solution is from about 1:1 to about 4:1.

30. The process of claim 21, wherein the reaction is conducted at a temperature in a range of about 0° to about 80° C.

31. The process according to claim 30, wherein the molar ratio of tosyl reactant to sugar alcohol is about 2:1 to about 4:1, the reaction is conducted at a temperature of about 15° to about 25° C., and at a pH of about 7.5 to about 10.5, and the organic solution of tosyl reactant is added to the sugar alcohol solution over a period of about 15 to about 45 minutes.

32. The process of claim 21, wherein the sulfonyl reactant is a tosyl chloride in a substantially water-immiscible organic solvent.

33. A product produced by the process of claim 21.

34. Sugar alcohols linked through either of their primary hydroxyl positions to one or more primary hydroxyl groups of sucrose, sugar alcohols, oligosaccharides, or polysaccharides and their lower molecular weight analogs.

35. The sugar alcohol according to claim 34 which is linked through either of its primary hydroxyl positions to either primary hydroxyl group of sugar alcohols selected from the classes consisting of the alditols and the pentitols.

36. The sugar alcohol, selected from the classes consisting of the alditols and pentitols, according to claim 34 which is linked through either of its primary hydroxyl groups to the 6- or 6' positions of sucrose.

37. The sugar alcohol, selected from the classes consisting of the aiditols and pentitols, according to claim 34 which is linked through either of its primary hydroxyl groups to one or more primary hydroxyl position of cyclodextrins.

38. The sugar alcohol, selected from the classes consisting of the alditols and pentitols, according to claim 34 which is linked through either of its primary hydroxyl groups to multiple primary hydroxyl position of polysaccharides selected from the group consisting of cellulose, amylose, amylopectin, chitosan and pullulan or their lower molecular weight analogs.

39. A process for the preparation of a poly-6-O-substituted-polysaccharide product which comprise slowly adding a sulfonyl halide dissolved in a substantially water-immiscible organic solvent to a polysaccharide dissolved in an aqueous alkaline solvent, wherein a reaction takes place at the interface of the aqueous solution and the organic solution, and maintaining favorable reaction conditions until the desired poly-6-O-sulfonyl-polysaccharide product is formed and recovered.

40. The process of claim 39, wherein the sulfonyl reactant is selected from the group consisting of tosyl chloride, mesyl chloride, trifyl chloride, trimsyl chloride, tripsyl chloride, or 1,1'-sulfonyl diimidazole.

41. The process of claim 39, wherein the sulfonyl reactant is a tosyl chloride in a substantially water-immiscible organic solvent.

42. The process according to claim 39, wherein the polysaccharide is selected from the group consisting of cellulose, amylose, amylopectin, pullulan and chitosan, or their lower molecular weight analogs.

43. The process according to claim 39, wherein the tosyl halide is dissolved in toluene, the polysaccharide is dissolved in dilute aqueous alkali hydroxide, the alkaline aqueous solution exhibits a pH of about 7.5 to about 10.5, the temperature is in the range of about 15° to about 25° C., and the product is recovered by centrifugation of the aqueous phase and dissolution in pyridine.

44. The process according to claim 39, wherein the tosylated polysaccharide is dissolved in dry pyridine and dry chloroform, the initial reaction temperature is below about −50° C. and which is eventually raised to a temperature in the range of about 15° C. to about 25° C. to complete the reaction.

45. The process according to claim 39, wherein the polysaccharide is alpha-cellulose, which is initially dissolved in an aqueous solution of 5% cadmium oxide in 28% ethylenediamine.

46. A process for the preparation of a poly-6-O-sucro polysaccharide which comprises adding an aqueous alkaline solution of sucrose to a poly-6-O-tosyl polysaccharide solution prepared according to the process of claim 39, and maintaining the reaction conditions until the poly-6-O-sucro polysaccharide is formed and recovered.

47. The process according to claim 46, wherein the polysaccharide is selected from the group consisting of cellulose, amylose, amylopectin, pullulan and chitosan, or their lower molecular weight analogs.

48. A process for the preparation of a poly-6-O-sugar alcohol polysaccharide which comprises adding an aqueous alkaline solution of a sugar alcohol to a poly-6-O-tosyl polysaccharide solution prepared according to the process of claim 39, and maintaining the reaction conditions until the poly-6-O-sugar alcohol polysaccharide is formed and recovered.

49. The process according to claim 48, wherein the polysaccharide is selected from the group consisting of cellulose, amylose, amylopectin, pullulan and chitosan, or their lower molecular weight analogs.

50. The process according to claim 49, wherein the sugar alcohol is selected from the groups consisting of the alditols and the pentitols.

51. A product produced by the process of claim 45.
52. A product produced by the process of claim 46.
53. A product produced by the process of claim 47.
54. A product produced by the process of claim 48.
55. A product produced by the process of claim 49.

* * * * *